United States Patent [19]

Sharp

[11] Patent Number: 4,713,963
[45] Date of Patent: Dec. 22, 1987

[54] METHOD AND DEVICE FOR VACUUM CHROMATOGRAPHY

[76] Inventor: Daryl Sharp, 317 Woodhaven, Chapel Hill, N.C. 27514

[21] Appl. No.: 879,022

[22] Filed: Jun. 26, 1986

[51] Int. Cl.[4] .......................................... G01N 31/08
[52] U.S. Cl. ................................................... 73/23.1
[58] Field of Search .......................... 73/23.1, 61.1 C; 55/270, 386; 210/656, 198.2

[56] References Cited

U.S. PATENT DOCUMENTS

| | | | |
|---|---|---|---|
| 3,398,505 | 8/1968 | Llewellyn | 55/16 |
| 3,712,111 | 1/1973 | Llewellyn | 73/23.1 |
| 3,936,374 | 2/1976 | Bradley | 210/31 C |
| 3,957,470 | 5/1976 | Dawes | 55/342 |
| 4,035,168 | 7/1977 | Jennings | 73/23.1 |
| 4,213,326 | 7/1980 | Brodasky | 73/23.1 |
| 4,432,225 | 2/1984 | Hayes et al. | 73/23.1 |
| 4,641,541 | 2/1987 | Sharp | 73/23.1 |

OTHER PUBLICATIONS

Elements of Flow and Diffusion Processes in Separation Nozzles, by W. Ehrfeld, vol. 97, section 8.3, Springer Tracts in Modern Physics, Springer Verlag Berlin, New York 1983.
Cramers, C. A., G. J. Scherpenzeel, and P. A. Leclercq; Increased Speed of Analysis in Directly Coupled Gas Chromatography-Mass Spectrometry Systems, J. Chromatography, 203 (1981): 207–216.
Trehy, M. L., R. A. Yost, and J. G. Dorsey; Short Open Tubular Columns in Gas Chromatography/Mass Spectrometry, Anal. Chem. 58 (1986): 14–19.
Sharp, D.; The Design and Evaluation of a GC/MS Interface (submitted for publication 10/86, Int. J. of Mass Spectrometry and Ion Processes).

Primary Examiner—Michael J. Tokar
Assistant Examiner—Hezron E. Williams
Attorney, Agent, or Firm—Lynn E. Barber

[57] ABSTRACT

A method and device for analyzing samples containing mixtures of organic compounds using vacuum chromatography is disclosed. The method and device are particularly useful for obtaining mass spectra for identification purposes. The method involves passing a sample dissolved in a solvent through a column with a carrier gas and depositing a thin layer of the sample in the interior of a short column. The short column is then attached to an MS interface. The device comprises a combination of a variable molecular separator and a column alignment component. The alignment component may also be used as a direct probe injector. This device and method allow the separation and MS analysis of mixtures of intermediate molecular weight compounds.

22 Claims, 9 Drawing Figures

METHOD AND DEVICE FOR VACUUM CHROMATOGRAPHY

FIELD OF INVENTION

The present invention relates to Gas Chromatography (GC) and more particularly to the combined methods and instrumentation for Gas Chromatography and Mass Spectrometry (GC/MS) and pertains to Vacuum Chromatography or Very Short Column Gas Chromatography/Mass Spectrometry (VSC-GC/MS).

Gas Chromatography is an analytical technique of separating a mixture of organic compounds according to their volatility. This is accomplished by injecting the sample dissolved in a solvent into a carrier gas stream (usually helium) which is passed through a long capillary column whose inner walls are coated with a thin liquid film. Careful control of experimental conditions such as carrier gas flow rate, column dimensions, temperature and liquid film thickness insures that the individual compounds separate into narrow discrete bands or "peaks" as they pass through the column for maximum separation or resolution from each other. Temperature programming as opposed to isothermal analysis counteracts the natural tendency of the bands to spread with time and produces uniformly shaped peaks across the entire chromatogram or graphical display of the analysis.

If the GC is connected to a mass spectrometer these individual compounds may also be identified by their unique mass spectra. This mass spectrum may be a graphical display of peaks representing the mass and intensity of characteristic fragments of the sample molecule. Thus, both separation and identification of individual components of a sample mixture may be accomplished in one continuous operation by combined GC/MS analysis.

This invention relates to a rapid and efficient method for the separation and MS analysis of high molecular weight compounds for which the conventional GC separation process becomes prohibitively long and the peaks become very low and broad with time, thus reducing sensitivity.

An obvious solution to the problem is to use shorter GC columns. The difficulty with this approach is that short columns are generally inefficient; that is they do not permit similar compounds or compounds with nearly the same molecular weight to be separated from each other.

It is the purpose of this invention to provide a device and method for gas chromatography using a very short GC column which may nevertheless be just as efficient as much longer and narrower capillary GC columns. This is accomplished by using the column with carrier gas pressure and flow conditions which are considerably different than those of conventional GC.

OBJECTS OF THE INVENTION

One object of the invention is to provide a versatile micro-scale vacuum lock/inlet system applicable to any sample regardless of its physical state and adaptable to most of the standard methods of introducing organic compounds into the mass spectrometer by either static or continuous flow means with all of the advantages which may be attributed to micro-scale quantitative analysis without exposure to chemically active surfaces.

Another object of the invention is to provide the means for an improved two-stage method of sample introduction, suitable for conventional vacuum exhaust GC/MS, for vacuum GC, or for direct MS analysis of solid samples.

Another object of the invention is to provide a means by which the carrier gas split between the MS and an auxiliary vacuum system (sepvac or SV) is conveniently and accurately controlled in a continuously variable range between zero and one hundred percent in a manner such that the primary gas flow has an unobstructed and unrestricted line of sight path to the MS without exposure to a chemically active surface.

Another object of the invention is to provide a method of conducting MS analysis which prevents the "overload" of the MS caused by introduction of too much of the sample to the MS at once.

Another object of the invention is to provide a method of analyzing samples dissolved in a solvent with an MS, without introducing the solvent into the MS.

Another object of the invention is to eliminate the problem of sample "hold-up" via condensation or chemical interaction between the sample and the surface of any interface between a GC and an MS.

Another object of the invention is to provide a means of sample enrichment of the GC carrier gas stream passing through the interface into the MS.

Another object of the invention is to provide an interface by means of which the pressure of the MS ion source may be conveniently and accurately controlled during the course of an analysis.

Another object of the invention is to provide an isolation valve by means of which either the GC or the MS may be operated independently of the other, including the ability to allow samples to be directly introduced into the MS ion source without disconnecting the GC.

Another object of the invention is to provide the means of connecting GC capillaries of any commonly used cross-sectional dimensions to a GC/MS interface so that both the GC and MS may be operated under their optimum conditions.

Another object of the invention is to provide the means of introducing solid samples for either vacuum gas chromatography/mass spectrometry or direct insertion or exposure mass spectrometry in a thin uniformly dispersed layer which insures a rapid and even response to temperature or gas flow changes as well as to direct or indirect sources of ionizing energy.

Another object of the invention is to provide the means by which the lateral and rotational position of the sample in the MS source may be conveniently controlled.

Another object of the invention is to provide a means for separating sample molecules which may be too nonvolatile, too chemically reactive or too temperature sensitive to be separated by conventional gas chromatography prior to analysis by the mass spectrometer.

Another object of the invention is to provide an improved vacuum lock device which may be much smaller than the prior art devices because it provides for the direct manipulation of the micro glass sample container (the fused silica column) and also provides the means to combine the isolation valve and auxiliary vacuum control functions.

Another object of the invention is to provide a special union by which a discardable retention gap or pre-column may be connected in front of a conventional capillary GC column so as to prevent the accumulation of undesirable sample residues with repeated use and to provide for the efficient injection of sample solvents with a minimum distortion of the peak shape of sample components.

Another object of the invention is to provide an interface which may function as a conventional supersonic jet separator under high viscous flow rate conditions in which a sample introduction capillary may be made to act as both a flow restrictor and a jet tip which may be adjusted to control the gap width.

Still other objects and advantages of the invention will become apparent to those of skill in the art after reading the following description of a preferred embodiment.

BACKGROUND INFORMATION

Purpose

The device and method of this invention for vacuum chromatography make possible the separation and MS analysis of high molecular weight and chemically reactive organic compounds without the problems found in the prior art. In particular, this invention overcomes the major problems for the analysis of this type of sample, found in direct inlet probe MS analysis high pressure liquid chromatography, traditional wide-bore column chromatography, and short column vacuum exhaust chromatography when operated in tandem with a mass spectrometer.

Direct Inlet Probe Analysis

Direct inlet probe analysis is a standard method for analyzing samples to obtain mass spectra. The sample is evaporated directly into the MS source from a cavity at the end of a long stainless steel rod or probe which is inserted through a vacuum lock in order to prevent disturbance of high vacuum conditions in the MS. Direct inlet probe analysis even with temperature programming, however, is not an efficient separation method. For this reason, it is only suitable for more or less pure compounds.

High Pressure Liquid Chromatography

Another method for analysis of sample mixtures of this type is high pressure liquid chromatography (HPLC). In this method, neither chemical reactivity nor high molecular weight presents a problem in the separation process. A major problem with HPLC is that because of the much larger amounts of solvent involved (principally water), the HPLC is much less compatible than gas chromatography with the high vacuum conditions required for the MS. In addition, these same sample characteristics present some problem in actually exposing the sample to the ionizing electron beam within the MS source because of active inlet and source wall surfaces.

Wide Bore Columns

When extra wide bore (0.053 cm inner diameter or ID) fused silica columns, which have recently become available, are coated with very thick liquid films and used with high carrier gas flow rates, they have chromatographic properties that are similar to very large diameter (2 mm ID) columns packed with solid adsorbent granules that were used prior to the use of fused silica columns. At low flow rates and with thinner films, higher resolution GC is also possible with these extra wide bore columns. The problem with these wide bore columns is that with current methods and instrument designs they would not allow efficient chromatographic separation under the flow and pressure conditions produced by a direct GC/MS connection.

Short Column Vacuum-Exhaust Chromatography

One significant problem with the prior art short column-vacuum exhaust systems as used with all but the newest MS instruments (which can resolve overlapping peaks), is a lack of GC resolution of the compounds resulting in overlapping peaks which cannot be resolved. In the vacuum chromatography of this invention, both rapid and efficient separation of higher molecular weight compounds can be accomplished although the inlet and outlet of the GC column are evacuated separately and the average column pressure is much lower than in short column-vacuum exhaust systems so that transition flow conditions, which are intermediate between viscous and free molecular flow, exist in the entire analytical column rather than just in the MS end of the column as for vacuum exhaust chromatography.

Another disadvantage of the short column-vacuum exhaust method is that the conventional on-column sample injection technique deteriorates under subatmospheric pressure inlet conditions resulting in further peak broadening effects. The problem has been avoided in this invention in the first step of the two-step sample introduction procedure which allows solvent injection to take place under atmospheric exhaust conditions. The second step of the two-step process permits the introduction of the solid sample in a uniformly dispersed but compact form amenable to efficient GC/MS separation and analysis.

RELATED PATENT APPLICATIONS

The preferred embodiment of this invention utilizes a GC/MS interface or variable molecular separator described in a previous patent application (Ser. No. 06/748,000 filed 6/24/85) which is summarized below and is incorporated by reference herein. The variable molecular separator serves as an interface between a gas chromatograph and a mass spectrometer. Sample enrichment effects and the GC carrier gas flow split between the MS and an auxiliary vacuum system are controlled by the depth of insertion of the end of the input column into the bore of a second short larger diameter capillary which serves both as a transfer column to the MS and as an extension of the analytical GC column. An important feature of this invention is the fact that the external outlet to the separator vacuum is so large in diameter in comparison to the inside diameter of the MS transfer capillary (typically forty or more times as large, or as required so that the dimensions of the vacuum outlet do not affect this flow split), that the dimensions of the external outlet do not affect the carrier gas split from the MS. This feature is completely different from any of the prior art.

A related patent application for an internal GC/MS interface (Ser. No. 06/828,178 filed 2/11/86), relates to an attachment which converts the standard MS source to a variable conductance source or an internal GC/MS interface. It comprises an interface which may be attached directly to an inlet probe which becomes aligned with the source as it is inserted into a mass spectrometer or it may be attached to the mass spectrometer source to align an inserted sample capillary. The sample goes directly into the source avity and an auxiliary vacuum is not required for sample enrichment.

For clarification, Table 1 is a tabular summary of the various configurations and applications of the three inventions.

SUMMARY OF THE INVENTION

Description of the Invention

The invention consists of a method and a device for separating unknown sample mixtures into their separate components prior to mass spectrometry. In the preferred embodiment, the device and method for performing a combined GC/MS analysis employ a short (20 cm) MS transfer capillary with an inside diameter of 0.053 cm which serves as the analytical GC column and which is coated on the inside with a liquid methyl silicone film 1.6 microns thick, which forms a chromatographic surface. The approriate film thickness and composition of the bonded liquid phase used in the analytical column will depend on the molecular weight range and polarity of the components of the sample mixture to be separated just as in conventional chromatography.

The device consists of a GC/MS interface described in the previous invention which encloses the GC column described above which is inserted directly into the MS source. Two guide rods are attached to this interface which serves to align a sliding union which connects a sample introduction capillary to a source of carrier gas through a long flexible capillary column and allows the sample introduction capillary to be inserted into the MS transfer capillary to some predetermined depth. In a completely separate step prior to the actual analysis the sample introduction capillary is prepared by using the sliding union to connect it to a standard GC on-column injector through a "retention gap" capillary followed by injection and deposition of the sample dissolved in a solvent by special GC injection techniques which will be described in detail.

Invention Method

The method of the invention is comprised of (1) a sample injection and deposition step with an intermediate operation where the sample introduction capillary is disconnected from the injection system and connected between the flow control column and the interface and (2) a sample introduction and analysis step. The first step of the method is nearly identical to the on-column injection technique for conventional capillary GC except that special precautions must be taken to ensure that the sample is confined to a narrow band in the end of the sample introduction capillary. A dissolved sample is injected into a long retention gap capillary connected to a sample introduction capillary, which in this step is left unconnected under atmospheric exhaust conditions just as for conventional GC and is not inserted into the mass transfer capillary. The use of the retention gap capillary allows the sample and solvent molecules to move rapidly through this section without encountering any chromatographically active surfaces. The purpose of the retention gap capillary is to prevent the sample zone from being as broad as the flooded solvent zone. Adjustments in the experimental conditions can be made to allow the initial sample zone to be confined to a narrow band located near the MS end of the sample introduction capillary and the solvent to escape. The length of the retention gap section of the capillary should be somewhat longer than twenty (20) cm per microliter solvent injected, which is the approximate length of the flooded section, to ensure that the flooded solvent is completely contained in a low or zero retention zone.

Temperature programming of the sample column up to the boiling point of the solvent during the first step at the time of injection may be used to further minimize the initial sample band width. Carrier gas flow rate is another parameter which may be quite different in the sample injection step as compared to the actual analysis in the two step process of the invention. The presence of a narrow section of the liquid phase coating at the MS end of the sample introduction capillary to absorb the sample along with the inclusion of a retention gap capillary of appropriate length reduces the extent of peak broadening before the actual analysis begins.

When used with a conventional GC column and with the short column of this invention, a retention gap capillary also extends the life of the column by preventing the accumulation of undesirable nonvolatile inorganic residues with repeated use.

After the sample has been deposited in a narrow layer in the end of the sample introduction capillary during the first step, the retention gap capillary is disconnected, and with the isolation valve closed, the sample introduction capillary with the samle deposited near the MS end is connected between a very long flow control capillary, which may be a conventional GC capillary column, and the interface by means of a sliding zero dead volume union (ZDV) and Vespel ferrules. In the second step, a slight opening of the isolation valve exposes these capillaries to the auxiliary vacuum which reduces the pressure to an acceptable level before the isolation valve is fully opened to expose the system to the still higher vacuum of the MS which is then only slightly disturbed or contaminated by outside air. The sample introduction capillary with the deposited solid sample is then inserted into the MS transfer column to a predetermined column exit position (CEP) for the analysis. The extra wide bore (0.053 cm ID) MS transfer column in the GC/MS interface is used as the primary analytical GC column instead of having it serve merely as a short extension of the very long (15 to 60 m) capillary GC column as it does for conventional GC with the interface. The conventional GC column is used here only to introduce and control the carrier gas flow to the short analytical column. An auxiliary vacuum system maintains a vacuum at all times.

During the second step of the method, control of the depth of insertion (or CEP), the carrier gas flow, and the rate of temperature programming of the interface column allow separation and identification of the components of the sample mixture. The CEP is measured from the orifice of the MS transfer capillary to the end of the inserted sample introduction capillary. The quantity (L-CEP) is the effective length of the analytical column, where L is the total length of the MS transfer capillary. Thus the effective length may vary from zero (direct MS probe analysis) to L. Higher carrier gas flow rates from the control column will be required for very low CEP values since most of the flow will go to the auxiliary vacuum rather than through the MS column, and pure molecular flow conditions will then also exist in the MS capillary. The volatility of the sample mixture will determine the length of the analytical column used for a particular analysis. The percent transmission of carrier gas through the interface can be determined exactly from the cross sectional dimensions of the annular space between the coaxial columns and the CEP (see previous two patent applications cited above). The flow rate can also be adjusted by changing the head pressure of the long capillary column or by changing to a column of different dimensions. For vacuum chromatography when the CEP is nearly equal to L, it may be necessary to use a very narrow or tapered MS transfer capillary in order to prevent both the occurrence of pure molecular flow conditions within the capillary and incomplete separation of mixture components as for direct insertion MS analysis. When the CEP is nearly equal to L and particularly for very high molecular weight compounds, a clear distinction can still be made between vacuum chromatography and direct insertion MS analysis depending on the carrier gas flow rate. Even in the absence of a carrier gas, the invention is an improvement over conventional direct insertion MS methods since the sample may be evaporated from the sample capillary at a point just adjacent to the electron beam within the source which minimizes sample contact with active metal surfaces prior to ionization.

Fine Tuning the Sample Injection and Deposition Step

The optimum analysis conditions for the first injection and deposition step of the method may be determined for any type of sample by doing preliminary experiments with the sample introduction capillary connected to a conventional GC detector in order to determine the position and width of the solvent and unseparated sample bands under a variety of carrier gas flow rates, temperature conditions, and solvent volumes. The sample introduction capillary may then be connected to the GC/MS interface for analysis of the sample. It is apparent also that the first sample injection step may be used to remove all but the most nonvolatile components of a sample mixture prior to vacuum chromatography or direct MS analysis. A satisfactory controlled sample deposition step as described above cannot take place under reduced or sub-atmospheric pressure conditions at the point of injection even using cryogenic techniques. This is the primary reason for the two-step process.

The length of the flood zone where the sample solvent is injected into the retention gap column is approximately 25 to 30 cm per microliter solvent injected provided the carrier gas flow rate exceeds 1.5 to 2 ml/min. The best temperature range is from approximately twenty degrees centigrade below the boiling point (BP) of the sample up to the BP. Deactivated fused silica is ideal for the retention gap column since its wettable surface also has low adsorption properties. Temperature programming over this range may also increase the efficiency of sample band reduction by the retention gap technique.

Fine Tuning the Sample Introduction and Separation Step

In addition to controlling the length of the MS transfer capillary and the CEP, programming of the carrier gas flow allows the precise control of the pressure necessary for reproducible analysis and efficient separation. This avoids pressure that is too low resulting im molecular flow conditions in the sample introduction capillary and migration of the sample molecules independently of the carrier gas through the MS transfer capillary according the their molecular velocities and their partial pressures. It also avoids pressures which are too high and cause viscous flow conditions. For transition flow conditions at intermediate pressures between these two extremes, the combination of a thin annular boundary gas layer moving at high linear velocities through the MS transfer capillary coated with a relatively thick bonded liquid film will provide the necessary conditions for efficient chromatographic separation of the strongly bound, relatively involatile sample molecules, comparable to that expected for conventional capillary gas chromatography. In general, the separation process should also take place at much lower column temperatures than for conventional capillary GC/MS.

Invention Device

The device consists of a vacuum tight sample introduction component and an interface connected in series along a common axis with the inlet port of the mass spectrometer. The interface also contains an isolation valve which allows the device to function as a vacuum interlock. One end of the sample introduction component is held within a sliding union component which controls the precise depth of insertion of a small diameter capillary column of the sample introduction component into a second larger diameter column contained in the interface. The sample introduction component used with the sliding union component serves both as a means of introducing a deposited sample to initiate the analysis and as a means of adjusting the length of the analytical GC column through which the sample must pass to reach the MS source (CEP).

The sliding union of the invention is improved by the use of a polyimide composite polymer (Vespel SP-3), designed especially for vacuum or dry applications where the filler is fifteen percent molybdenum disulfide. This should prevent the Vespel adapter and ferrule from sticking to the capillary after exposure to high temperatures which is a problem with the prior art using pure polyimide (SP-1) or the fifteen percent graphite composite (SP-21). The use of the standard commercially available zero dead volume (ZDV) union is limited to connecting capillaries with the same inner diameter (ID) as the inner bore of the union, or in the case of the through bore union, to capillaries with the same ID. When the capillaries are of different ID, a short nickel insert with a tapered bore to match the ID of the two capillaries being connected, may be used to provide a continuous chromatographic surface through the sliding union with a minimum of distortion of gas flow and chromatographic properties. The nickel surface of the tapered bore may be made just as chemically inactive as the fused silica GC capillaries and may also have as good or superior characteristics for bonding or coating with cross-linked liquid films. The union of this invention, rigidly fixed to the cage support of the coiled column, also offers a convenient means of connecting the fragile coiled conventional GC capillary column to the injector without uncoiling or handling the analytical column itself. Also, the original exact length of the conventional GC column as specified by the manufacturer is preserved along with the evenly cut manufactured ends of the fused silica column and its polyimide coating.

A permanent ZDV union can be constructed using a very short section of thin walled tapered nickel capillary with a slot at each end to fit exactly the fused silica capillaries being connected. A polyimide resin in the liquid form is then built up in successive layers by high temperature curing (about 250 degrees C.) so that the cured polymer bonds permanently to the polyimide protective coating of the fused silica capillaries, thereby completely enclosing and mechanically stabilizing the thin walled nickel capillary. This union should be much more effective in preventing sample contact with any nonchromatographic surface or sealant. This union should also have the advantage of a much lower thermal mass than the standard ZDV union so that the development of a cold spot during fast temperature programming is avoided.

This very short column or vacuum chromatography invention is clearly distinguished from conventional atmospheric outlet gas chromatography, vacuum exhaust gas chromatography, [15 to 60 m columns] or the recently developed GC/MS method using short fused silica columns under vacuum exhaust conditions (short column-vacuum exhaust), in that in the invention, the entire separation process takes place at reduced pressures which for vacuum exhaust chromatography only occur at the very end of the GC column. This difference is in addition to (1) the difference in column length, with that of the invention being 20 cm or less or compared to a meter or more for the prior art methods and (2) the difference in column internal diameter, with that of the invention being at least 0.053 cm, as compared to 0.032 cm or less for a conventional column.

Applications of the Invention

The device of the invention should be useful for a wide range of organic compounds, from those compunds which are gases under ambient conditions to those which have almost negligible vapor pressure at the maximum temperature of the MS source which is about 350 degrees C. In combination with the GC/MS interface, the invention is in effect a very versatile micro vacuum lock with the same functions as the much larger standard vacuum lock/solid sample introduction port that provides for greater utilization of micro samples with all of the analytical advantages associated with micro analysis. The device of the invention may be used in a number of applications, in addition to the method described here, which are summarized in Table 1. These include use in a conventional direct connection GC/MS where the end of the long GC capillary is fed through both components of the interface directly into the MS source and the positioning device is used to determine the exact position of the end of the GC column with respect to the ionizing electron beam.

The invention is also particularly useful for direct probe analysis of samples with very slight, almost negligible vapor pressure where the solid sample in the form of a thin film in the end of the sample introduction capillary is inserted just adjacent to the electron beam in the source. The sample may also be deposited on a flattened or spatula tipped fused silica or nickel capillary or rod of similar diameter which can be inserted into the MS in the same way.

The invention may also be used for direct exposure analysis where a surface covered with a very thin layer of sample is directly exposed to an ionizing beam. Surface ionization techniques may be carried out with the insulating surface of a fused silica capillary or rod using photons in the form of a laser beam or a beam of neutral molecules (fast atom bombardment). The use of the electrically conducting nickel capillary or rod would permit direct surface ionization by an electron beam for secondary ion mass spectrometry (SIMS).

In addition, the invention may be used in flow splitting and/or for conventional molecular enrichment GC/MS by offering a convenient means of adjusting the column exit position (CEP) to a precise value along the length of the MS transfer capillary in order to adjust the carrier percent transmission and/or the enrichment factor as required when the GC flow exceeds the pumping capacity of the MS.

The ZDV sliding union has another useful application. Frequently a trace component must be detected and identified in a sample containing many other components of much higher concentration. The analysis of such a sample mixture in a quantity sufficient for the detection and identification of the minor components on a column may overload the capacity of the column and destroy peak shape and resolution which may well obscure the trace component. Splitting the sample at the injection point lowers the trace component below the detection level. A practical approach to the problem is to analyze the sample mixture on a high capacity column which still has sufficient resolution to isolate the trace component. The analytical characteristics of these recently introduced extra wide bore (0.053 cm ID) fused silica columns are unique for this purpose. This invention provides the means to connect such a column to the MS with the interface and the sliding union of the column position mechanism and to reduce the very high effluent flow rate to acceptable levels for the MS.

Another advantage of the invention is that a quantitative sample split in the interface at the end of the GC column is more accurate and reliable than an injector split of the prior art. An injector split is unreliable for two reasons. First, the actual split of the carrier gas is uncertain and must be determined by continually measuring the split flow. Second, the quantitative split of a sample of uncertain volatility is never reliable in a typical flash injector. Sample splitting from an ambient temperature on-column injector is not feasible. More importantly, a split that occurs in the interface may be varied accurately during the course of the analysis depending on the retention time(s) of the GC peak(s) of interest and any components in high concentration which may be diverted from the MS or quantitatively reduced to measurable levels. There are several possible means of electronically controlling the position of the GC column in the interface (CEP) depending on the accuracy and range required for the application.

The invention may also be used in continuous flow gas analysis as a means of accurately adjusting the interface of the invention described in the previously filed patent application for a variable molecular separator (above) so as to provide accurate flow control, stream splitting and molecular enrichment of trace constituents using a long fused silica capillary of various dimensions connecting the interface with a high pressure gas source reservoir. This reservoir may be the ambient atmosphere or a high volume flow stream.

A special modification of the interface, in which the MS transfer capillary is very short (less than 3 cm) and the interface becomes a small direct attachment to the source itself, can be used in some slightly modified form for all of the applications mentioned here and in the previous patent application referred to above. It can, however, only be used with any great advantage in mass spectrometers having relatively high pumping capacities, unless additional modifications are carried out to increase internal MS pumping efficiency.

The union has many uses both in its regular form and as a sliding union in conjunction with the alignment component. As a sliding union in conjunction with the alignment component of the invention the union may be used for the following purposes:

(1) Connection of the sample introduction column to the retention gap capillary.

(2) Alignment of the sample introduction column with the MS transfer column in the interface.

(3) Connection of the sample introduction column to the flow control column.

(4) Allowing the sample introduction column to be moved along its axis to control the extent to which it is inserted into the MS transfer column.

(5) Attaching short sections of columns with different cross sectional dimensions to the end of the conventional GC column in the interface for a wide variety of analytical purposes as summarized in Table 1 in addition to the vacuum chromatography method of the invention.

As a simple union (either the standard form with a nickel insert or as permanent single piece nickel construction) the union has many uses such as:

(1) Connecting GC columns with different liquid phases for multi-dimensional and network GC analysis.

(2) Connecting short protective columns to the front and end of conventional GC columns to preserve the original accurate length of the column.

(3) Attaching retention gap capillaries to conventional GC columns.

(4) Repair of broken GC columns.

DESCRIPTION OF THE PREFERRED EMBODIMENTS

Figure 1:
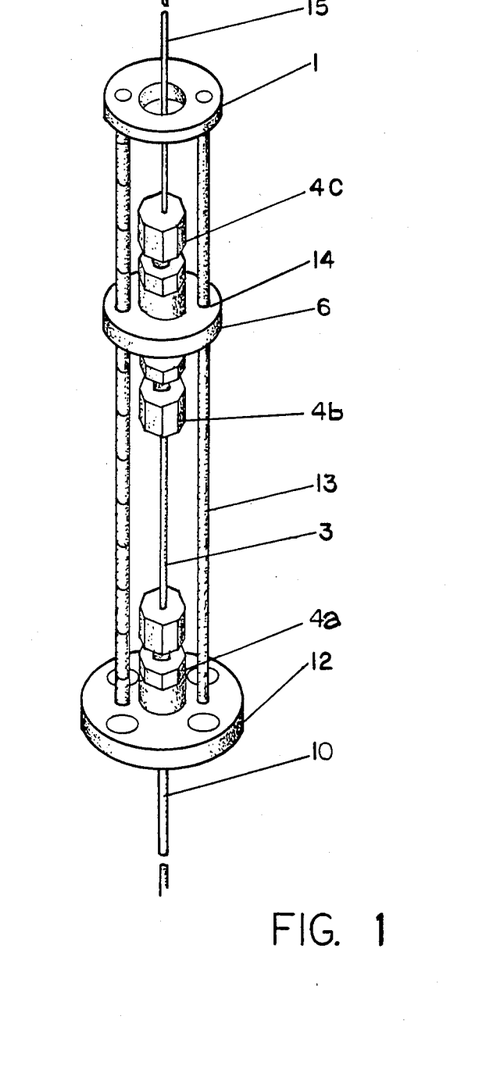
FIG. 1 is a perspective view of a preferred embodiment of the sample positioning component of the invention.
Figure 2:
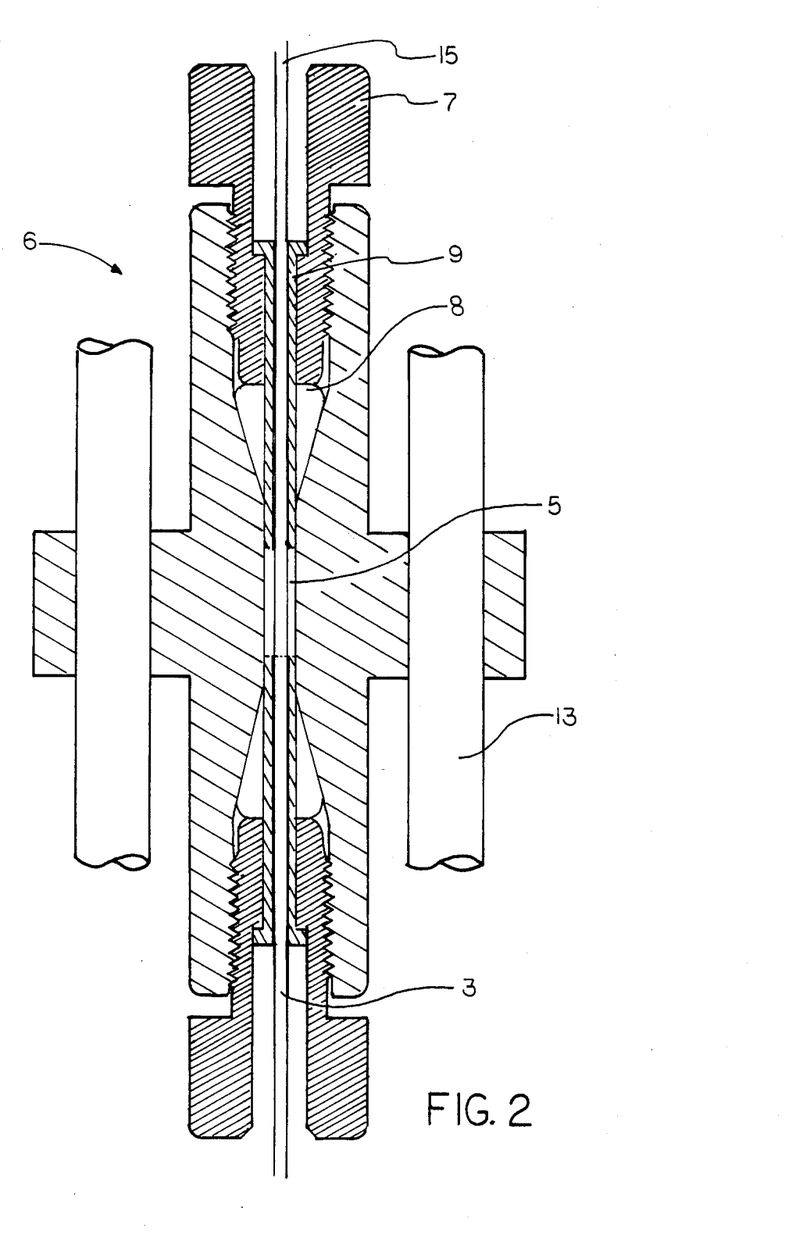
FIG. 2 is an expanded cross-sectional view of the sliding union of the preferred embodiment of the sample positioning component of the invention.

The device for vacuum gas chromatography or very short column chromatography comprises a sample positioning component, shown in FIGS. 1 and 2. The sample positioning component may be used with either the simplified or more elaborate interface, shown in FIGS. 4 and 5, respectively. In the sample positioning component, a sample introduction capillary 3 is held in place at one end by a first standard zero dead volume (ZDV) fitting 4a and at a second end by a second standard ZDV fitting 4b. The second standard ZDV fitting 4b and a third ZDV fitting 4c make up the modified 1/32" union which is the sliding union 6. The first ZDV fitting 4a is attached to a vacuum flange 12. The sliding union 6 allows adjustment of the position of the sample introduction capillary 3 within the mass transfer capillary 10. Guide rods 13 extend from a guide rod support piece 1 through a guide holes 14 in the sliding union 6 to the vacuum flange 12 and serve to strengthen the sample positioning component and to align the ZDV fittings 4a and 4b at each end of the sample introduction capillary 3. The guide rods 13 may have graduation marks in fractions of a centimeter so that the position of the sample introduction capillary 3 relative to the orifice of the MS transfer capillary 10 may be accurately determined.

The vacuum flange 12 may be used to attach the sliding union 6 to the interface of the previous invention, the variable molecular separator, (FIG. 7) replacing a similar flange/ZDV union. Alternatively, using a simplified version of that interface (see below, FIG. 4), the guide rods 13 may be attached directly to the interface. The vacuum seal ZDV fitting of the interface then becomes the first ZDV fitting 4a of the sample positioning component in FIG. 1. A long capillary 15 (15 to 60 m) which may be the analytical GC capillary or may simply function here as a flow control capillary is connected to the sliding union 6 by means of the third ZDV fitting 4c. The interior dimensions of the sliding union 6 may be modified depending on the application and the care required to join long capillary 15 (either a flow control capillary or analytical capillary) and the sample introduction capillary 3.

This invention would also be useful for conventional GC analysis in which it may be convenient to use a nickel extension section (not shown) to the long capillary 15 (analytical GC capillary) in much the same way as the sample introduction capillary 3 is used in the sample positioning component of FIG. 1, when optimized performance of the interface is required. Very thin walled electro-formed nickel capillaries with precise dimensions and perfectly square-cut ends are now commercially available which allow more precise alignment of the capillary in the interface gap and within the MS transfer capillary than with fused silica capillaries which are difficult to cut perfectly square ends. This short nickel section could also be attached more permanently to the sliding union 6. Nickel GC capillary columns with chemically bonded liquid phases are also now commercially available.

FIG. 2 shows an enlarged view of the sliding union 6 of the sample positioning component in which the sliding union 6 is a standard union fitting with a straight through bore. As shown in detail in FIG. 2, a nut 7, a Vespel ferrule 8, and adapter 9 allow the sample introduction capillary 3 to be firmly positioned. A similar nut, ferrule and adaptor combination (not shown) is used with each ZDV fitting. The sliding union 6 allows adjustment of the position of the sample introduction capillary 3 within the MS transfer capillary 10 by movement of the sliding union 6 along the guide rods 13. Inside the sliding union, the sample introduction capillary 3 and the long capillary 15 are butted against an inner insert 5, the ends of which insert 5 should be tapered if the capillaries are of different inner diameters (ID) so that the insert ends are of the same ID as the fused silica capillaries which butt against them. Interchangeable nickel inserts 5 can be used which have tapered bores whose two opposite orifices should exactly fit the ID's of the capillaries 3 and 15 to be connected. If the two capillaries 3 and 15 to be connected have the same ID, the may be inserted through appropriate Vespel adapters 9 and along with the adapters may be butted against each other without use of an inner insert 5. Another improvement is that the Vespel adapters 9 may be made from SP-3 Vespel rather than SP-1 or SP-21. This polyimide composite is composed of fifteen percent molybdenum disulfide which is designed specifically to give increased lubrication to sliding seals under vacuum conditions. For this application, it permits the nut 7-ferrule 8-adapter 9 assembly to be taken apart after exposure to high temperatures under compression, which cannot be done using either SP-1 or SP-21. This also permits the adapter 9 to be bored to have a much tighter fit with the fused silica capillary along its entire length thus requiring less external pressure for a good seal.

Use of the sliding union 6 allows a type of connection which should have very little detrimental effect on GC peak shape and should permit analytical GC capillaries (long capillaries 15) with a wide range of cross-sectional dimensions to be used with a minimum disturbance of uniform carrier gas flow through the connection beyond that expected for a gradual change in column dimensions. This union connector depends on the fabrication of a short accurately tapered nickel insert which may also be coated with a chemically bonded liquid film similar to that of the long capillary 15 to be connected.

This sliding union 6 should even permit the connection of an extra wide bore (0.053 cm ID×0.071 cm OD) GC column currently being used for high capacity separations (equivalent to a packed column) to the interface. Under these conditions (10 to 30 sccm), accurate split control is still possible according to the previous invention. This mode of operation should provide a good test of molecular enrichment effects for this type of interface under viscous and supersonic flow conditions as for a conventional jet separator in addition to serving a very practical analytical purpose.

Figure 3:
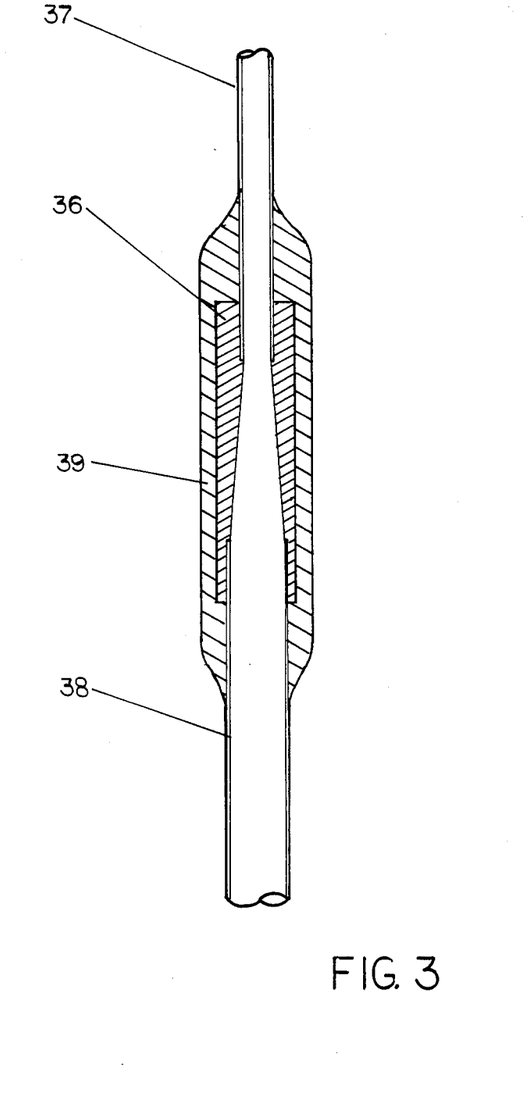
FIG. 3 is a cross-sectional view of a permanent zero dead volume (ZDV) union which is an alternate form of the union of FIG. 2.

A cross-sectional view of a permanent ZDV union is shown in FIG. 3. A short section of a tapered nickel capillary sleeve 36 has inlet slots that fit the fused silica capillaries 37 and 38 to be connected exactly. A cured polyimide resin layer 39 bonds to the polyimide coating of the fused silica capillaries 37 and 38 and encloses and mechanically stabilizes the nickel capillary sleeve 36.

Figure 4:
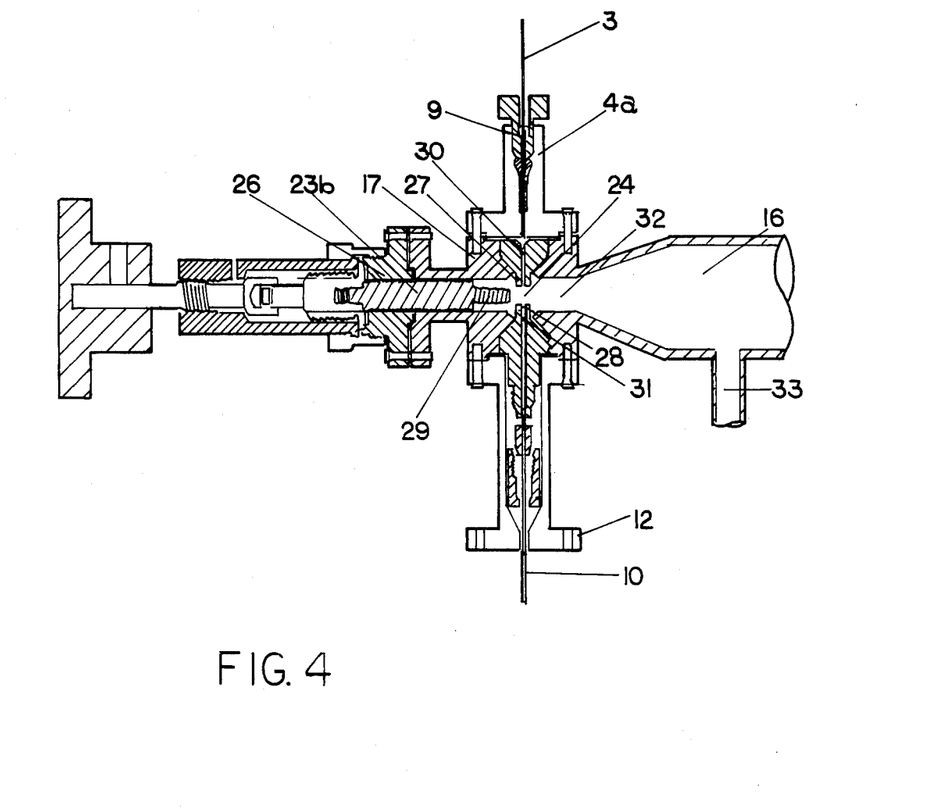
FIG. 4 is a cross-sectional view of a more elaborate version of the previous invention for a variable molecular separator which has replaceable, modifiable components to which the sliding union mechanism of this invention may be attached.
Figure 5:
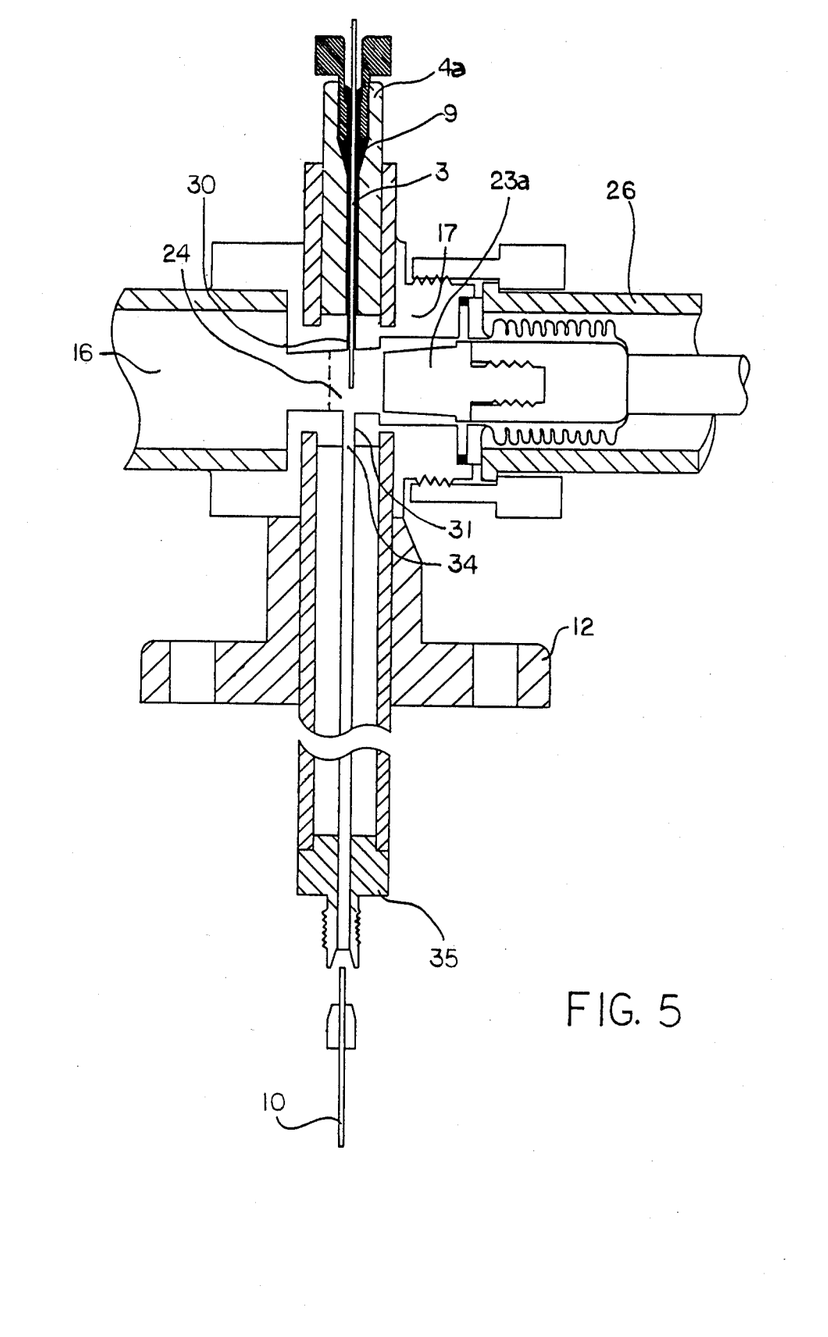
FIG. 5 is a cross-sectional view of a simplified version of the previous invention for a variable molecular separator.

The GC/MS interface used with the very short column analytical device of the invention is shown in detailed cross-section for the different versions in FIGS. 4 and 5. The interface may be the variable molecular separator described in detail in the previously submitted patent application (Ser. No. 06/748,000, above) in which case the GC carrier gas flow split between the MS and the auxiliary vacuum system 16 may be controlled by the depth of the insertion of the sample introduction capillary 3 into the MS transfer capillary 10 (FIG. 4). The interface may also be in a modified shortened form in which it is attached directly to the MS source and for which no auxiliary vacuum system 16 is required (not shown). With this internal source attached interface, the MS vacuum pumping system maintains the vacuum. In either case, the MS transfer capillary 10 extends into the MS source cavity 11 as discussed below.

In the interfaces shown in FIGS. 4 and 5, a valve stem 23a within the GC/MS interface may be shut as the sample introduction capillary 3 is withdrawn from the interface in the process of removing the sample introduction capillary 3 from the interface so that the vacuum is not disturbed. A vacuum cap (not shown) replaces the nut 7 and ferrule 8 on ZDV fitting 4a of the sample introduction component (see FIGS. 1 and 2, above) when the inlet is not being used.

Depending on the particular capillaries involved, more or less alignment and fit tolerance will be required of the tubes or channels in the interface through which the capillaries are inserted. A general requirement is that a fused silica capillary with a 0.040 cm outside diameter can be inserted into a second capillary with a 0.053 cm ID across a 0.6 cm interface gap 24, without obstruction at the orifices. A smaller interface gap 24 will permit the use of a MS transfer capillary 10 with a smaller ID. The design of a first embodiment of the interface and isolation valve of the variable molecular separator provides the means for a high conductance separator vacuum outlet to be connected to a high speed vacuum pump so that the gap can be made very narrow and permit an even closer fit of the inserted capillary.

As shown in both FIGS. 4 and 5, a standard bellows valve drive assembly 36 with a ¼ inch range is used to position the Vespel (SP-1) valve stem 23a (FIG. 5) or 23b (FIG. 4) in the interface gap 24 to function as to function as an effective GC/MS isolation valve. In one version of the interface (FIG. 4), a different valve stem 23b, is used for each set of removable jets A and B, 27 and 28, depdnding on the width of the gap between them. The Vespel stem (SP-1) insert tip 29 may be shaped to best fit the requirements of an isolation valve in different systems. It is not necessary that the isolation valve be an absolute high vacuum seal against atmospheric pressure in order for it to function effectively in this design. A short very thin vertical slot on the extreme end of the stem insert on the GC side (not shown) permits GC flow to continue uninterrupted when the orifice on the MS side is just sealed. The remaining upper portion of the GC side of the Vespel stem insert tip 29 is very slightly tapered to allow the Vespel to conform to the shape of the jet A 27 surface when used and to function as an effective isolation valve when the valve is fully closed. As shown in FIG. 4, the two jets 27 and 28 also provide the guide channels 30 and 31 for the respective sample introduction capillary 3 and fused silica MS transfer capillary 10. These guide channels 30 and 31 will be drilled to fit the outer diameter of the capillaries as closely as possible. The Vespel adapter 9 of the ZDV fitting 4a is also drilled to fit each individual sample introduction capillary 3 (or analytical capillary 15 for conventional GC) that is used. The interface gap 24 may be made very narrow provided there is sufficient auxiliary pumping capacity. The diameter of the outlet tube 32 to the auxiliary pump is large enough so that a high speed pump can be effective in producing low pressures in a very narrow interface gap 24 and is so large in comparison to the ID of the MS transfer capillary 10 that the flow split between the MS and the auxiliary vacuum depends solely on the dimensions of the two fused silica capillaries involved, the sample introduction capillary 3 and the MS transfer capillary 10. The gap pressure must always be very low compared to the pressure within the MS transfer capillary 10 in order to insure proper function of the interface as a flow splitter. A sidearm tube 33 provides a connection to a vacuum gauge. A narrow interface gap 24 improves the precision with which the sample introduction capillary 3 can be aligned with the orifice or the MS transfer capillary 10. With a 1 or 2 mm gap, the width of the annular space between the MS transfer capilalry 10 and the sample introduction capillary 3 can be reduced to less than 0.1 mm. In general, a very narrow annular space between the capillaries improves the performance characteristics of the interface. A vacuum flange union 12 serves to connect the interface to the MS. The primary purpose of this interface is to provide the maximum flexibility in changing the geometry of the interface as well as the operating conditions for research and development purposes as well as expanding the range of analytical applications.

A cross-sectional view of the simpler version of the external interface of the variable molecular separator is shown in FIG. 5. The interface is built around a modified bellows valve drive assembly 26 with a standard valve drive mechanism in which the standard valve stem is replaced by a Vespel stem 23a. Capillary guide channels 30 and 31 are drilled directly in the body of the isolation valve 17. The ZDV fitting 4a serves as an extended guide for the sample introduction capillary 3 as well as a means of securing its position and maintaining a vacuum seal as the position of the sample introduction capillary 3 is changed. A stainless steel needle capillary 34 serves as an extended guide for the MS transfer capillary 10 which is secured by a standard 1/16" swagelock fitting 34. A vacuum flange 12 serves to attach the interface to the mass spectrometer.

Figure 9:
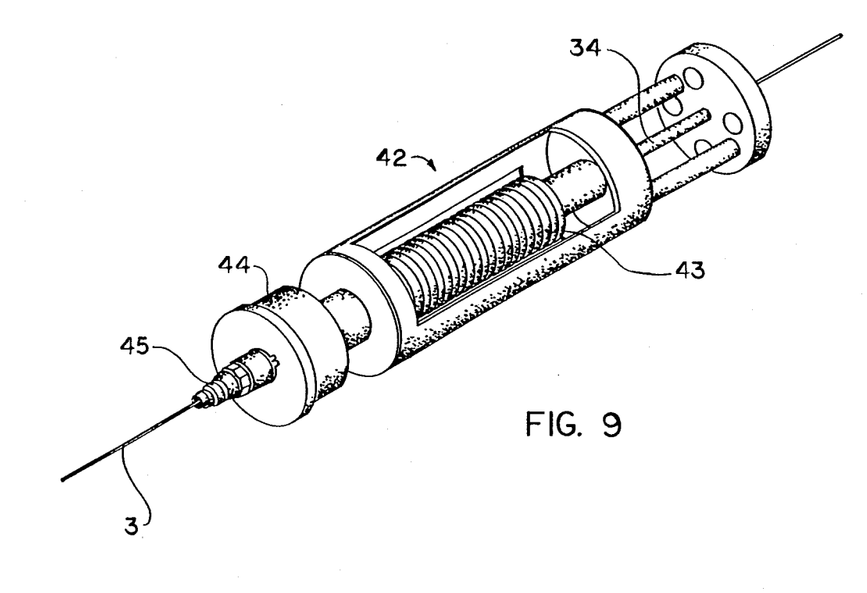
FIG. 9 is a perspective view of a bellows/micrometer drive mechanism.

The bellows/micrometer drive mechanism 42 which may be used to control the CEP is shown in FIG. 9. This component which may be controlled by a very accurate electronic stepper motor (not shown) is comprised of a vacuum bellows 43 attached to a micrometer drive assembly 44 to which the sample introduction capillary 3 is secured by means of a standard ZDV fitting 45. This component permits the CEP to be controlled over a range of 1.5 cm with 0.05 mm increments. It is particularly useful for the internal interface of the previous invention (FIG. 4) because of its accuracy over a relatively short range. It may be used in a number of different configurations depending on the application (see Table 1).

Figure 6:
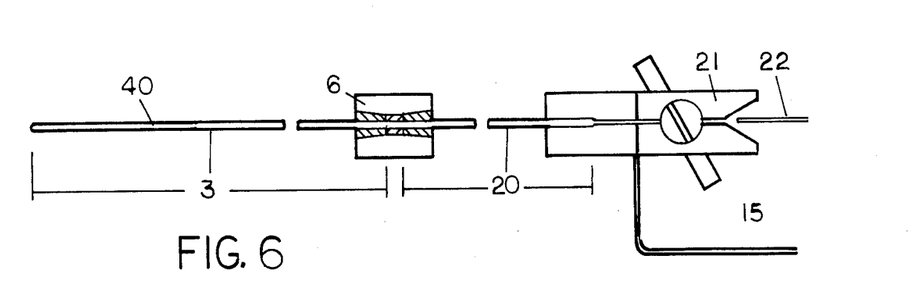
FIG. 6 is a diagrammatic representation of the first step of the two-step sample analytical method of the invention in which the sample introduction capillary is connected to the on-column injector through the retention gap capillary.
Figures 7, 8:
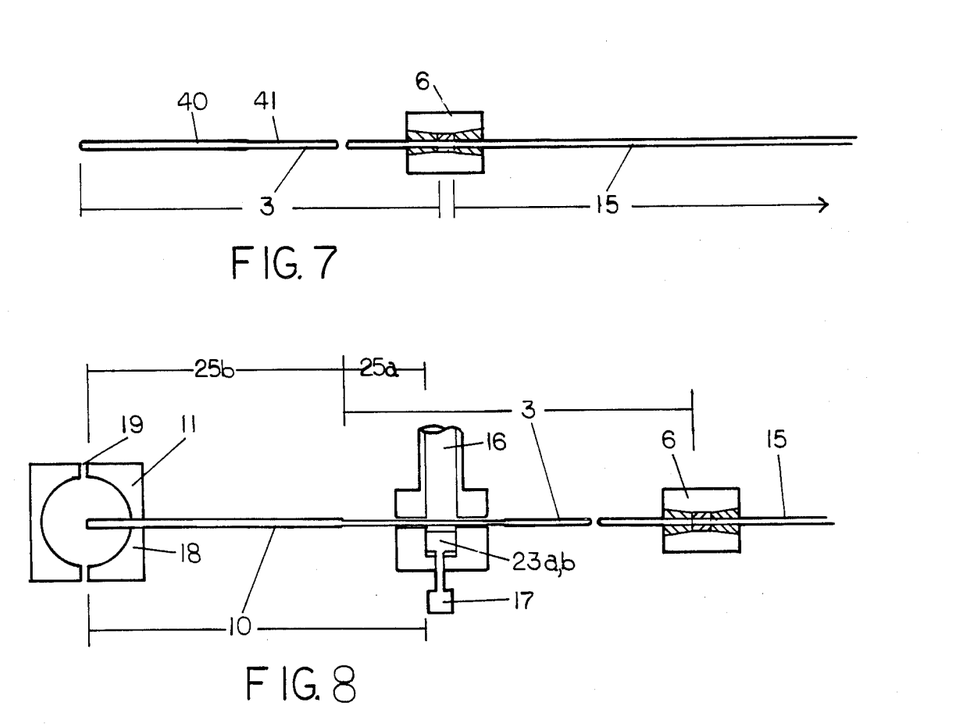
FIG. 7 is a diagrammatic representation of an intermediate operation in which the sample introduction column is disconnected from the retention gap capillary and on-column injector and connected directly to the flow control capillary by means of the sliding union.
FIG. 8 is a diagrammatic representation of the second step in the analytical method of the invention in which the end of the sample introduction capillary containing the deposited sample is connected to the interface and inserted into the MS capillary to begin the analysis.

In the method of the invention, a two-step sample introduction process is carried out as illustrated schematically in FIGS. 6-8. In FIG. 6, a short sample introduction capillary 3 which should be slightly longer than the MS transfer capillary 10 is connected to the sliding union 6. At this time, the MS end (bottom of FIG. 3) of the sample introduction capillary 3 is left unconnected. A 15 to 40 cm uncoated capillary functioning in this case as a "retention gap" capillary 20, which may have the same cross-sectional dimensions as an analytical GC long capillary 15, is connected to a conventional on-column injector 21 at one end and to the sliding union 6 at the other end in the usual manner. The retention gap capillary 20 is designed to contain the entire flooded zone resulting from the injection of the sample solvent from a syringe fitted with a long thin fused silica needle 22 to permit the sample to be deposited in a dispersed sample layer 41 (FIG. 7) on the liquid film coating 40 near the MS end of the sample introduction capillary 3 as discussed in detail in the background section. The flooded zone is typically 15 cm per microliter solvent at appropriate carrier gas flow rates and column temperature. After the solvent escapes from the sample introduction capillary 3, the carrier gas flow is stopped The retention gap capillary 20 is replaced by a long capillary 15 for flow control which is connected to the sliding union 6 by a ZDV fitting (not shown in FIG. 7). The MS isolation valve is then checked to determine that it is shut. The uncoated end of the sample introduction capillary 3 is then connected to the first ZDV fitting 4a. After a short period of time to allow the capillaries to be evacuated by the auxiliary vacuum system 16 of the interface, the isolation valve is opened by withdrawing the Vespel valve stem 23a (or 23b, above). The sample introduction capillary 3 is inserted to a predetermined depth into the MS transfer capillary 10 which has been previously inserted into the source cavity 11 through the MS source body 18 of a standard MS. The electron beam openings 19 define the path of the sample ionizing beam in the MS source cavity 11 (FIG. 8). The depth of insertion of the sample introduction capillary 3 into the MS transfer capillary 10 (CEP 25a) determines the analytically effective length 25b of the MS transfer capillary 10 which is that portion of the MS transfer capillary 10 between the end of the sample introduction capillary 3 and the MS source. The CEP 25a also determines the flow split or the amount of carrier gas flowing through the MS transfer capillary 10 to the MS. It will be convenient to start the carrier gas flow at the appropriate rate and allow the system to equilibrate before beginning the analysis since at low temperatures, the sample band will not move appreciably in the sample introduction capillary 3. The program to raise the temperature of the MS transfer capillary 10 at a fixed rate to a predetermined level is then initiated and the analytical separation process begins.

TABLE 1
SUMMARY OF ANALYTICAL METHODS AND PREFERRED MODES OF OPERATION

| Application | Interface | Analytical Method | MS Inlet | Sample | MS Carrier gas Control | Analytical Procedure | Method of Introducing Sample &/or Controlling CEP |
|---|---|---|---|---|---|---|---|
| 1 | B | VSC-GC/MS or vacuum chromatography | A | solid, as thin layer deposit | any combination of 1. head pressure 2. dimensions of long capillary 3. CEP | sample retained at end of sample introduction capillary by on-column injection using "retention gap" pre-column techniques followed by solvent-less sample introduction, adjustment of CEP, and temperature programming of source | sliding union controls CEP and permits sample introduction into internal interface attached directly to MS source (B); external interface (1A) functions only as vacuum lock inlet short nickel or fused silica sample introduction capillary, |
| 2 | C | VSC-GC/MS or vacuum chromatography | D | same as #1 | same as #1 | same as #1 except both probe and source temperature must be controlled | sliding union mechanism attached to ⅜" OD probe rod and interface, device must be inserted through standard vacuum lock for each analysis |
| 3 | A | VSC-GC/MS or vacuum chromatography | A | same as #1 or liquid film | same as #1 | same as #1, except that the long MS transfer capillary of this interface permits separation of more volatile compounds | same as #1 and #2 but analytical column is MS transfer capillary in external interface (A), whose temperature may be controlled independently of MS source |
| 4 | A,B, C | direct insertion | A,D | same as #1 | optional with or without gas flow | same as #1, 2, and 3 except sample introduction capillary inserted to end of MS transfer capillary adjacent to electron beam | same as #1, 2 or 3; sample diffuses into path of electron beam; prior controlled deposition of sample in thin layer insures rapid and uniform diffusion in response to source temperature change for greater sample utilization and analytical sensitivity |
| 5 | A,B, | direct exposure, surface ionization techniques | A | thin layer spot from solvent evaporation or same as #1 | carrier gas optional | sample probe is a fused silica rod with spatula or diagonally cut capillary Accurate positioning of sample required with respect to laser, molecular, or electron beam | micrometer/bellows drive attached to external interface for accurate translational and rotational control of probe or capillary in MS source; nickel or fused silica probe or capillary depending on ionization method and interface; this applies to #4 also |
| 6 | C | direct exposure | D | same as #5 | carrier gas optional | same as #5 | micrometer/bellows drive attached directly to probe |
| 7 | A,B, C | conventional capillary GC | A,D | dissolved in solvent | capillary GC column 15-60 Meters .02-.035 cm I.D. | all conventional capillary GC/MS methods; ZDV union may be used to attach "retention gap" pre-column in front of analytical GC column for "high performance" GC analysis | sliding union with conventional GC capillary attached to short nickel or fused silica capillary of special dimensions for optimized split enrichment characteristics |
| 8 | A,B, C | conventional, extra wide bore capillary GC/MS, | A,D | same as #7 | capillary 10-30 Meters .053 cm I.D. | interface necessary for flow split and/or sample enrichment | sliding union used to attach wide bore capillary to narrow bore interface position control capillary for split control or two stage external/internal GC/MS interface |

TABLE 1-continued

SUMMARY OF ANALYTICAL METHODS AND PREFERRED MODES OF OPERATION

| Application | Interface | Analytical Method | MS Inlet | Sample | MS Carrier gas Control | Analytical Procedure | Method of Introducing Sample &/or Controlling CEP |
|---|---|---|---|---|---|---|---|
| | | where column is much longer than for VSC-GC/MS | | | | | any of above with very high GC flow rate and restrictor end capillary; interface may function as conventional supersonic jet separator |
| 9 | A,B, C | continuous flow gas analysis | A,D | gas, vapor as trace quantities in air or other gas | same as #1 | continuous flow carrier gas or air from constant pressure reservoir or macro sample stream; interface permits split over wide range with molecular enrichment, diversion or complete isolation | same as #8 |
| 10 | A,B, C | direct connection capillary GC/MS | A,D | same as #7 | reduced GC flow required | same as 7 except head pressure must be reduced; limited to long (≧30 cm) narrow bore capillaries | GC column end inserted all the way through interface into MS source |
| 11 | A,B | 2-stage molecular enrichment GC/MS | A | gas or dissolved in solvent | same as #1, CEP 1st stage only | external and internal interfaces serve as 1st and 2nd stage molecular enrichment interfaces | variable CEP in 1st stage; fixed CEP in 2nd stage; transfer capillary of 1st stage becomes inlet capillary of 2nd stage |
| 12 | B,C | pulse flow GC-FT/MS | A,D | same as #1 | same as #1 | oscillating CEP produces pressure pulse in MS source synchronized with source ionization and ion storage cycle | oscillating linear drive solenoid - several modes possible depending on CEP range |
| 13 | A | short column GC/MS | A | high molecular wt in solvent | CEP only | same as conventional GC/MS except analytical column is only approximately 1 meter long | sample injection with atmospheric pressure exhaust then connection to external interface for CEP and split control and vacuum exhaust GC/MS analysis |

FOOTNOTES
1. A: External interface/variable molecular separator; B: Internal source attached interface; C: Internal probe attached interface.
2. Vacuum Chromatography/Mass Spectrometry or VSC-GC/MS
3. A: Micro-vacuum lock interface or any variation thereof (FIGS. 6 and 7); D: Standard vacuum lock
4. Sliding union of the invention for very short column GC/MS analysis (FIG. 2)
5. CEP: column exit position
6. Distinction between direct insertion and direct exposure techniques may be minimal using diagonally cut fused silica capillary and carrier gas flow

I claim:

1. A device for analysis of a sample using a mass spectrometer and a sample introduction column, said sample introduction column having a first end and a second end, said sample being deposited in a thin film on an adsorbent coating on the interior of the first end of the sample introduction column comprising:
   (a) an MS transfer column having a bore greater in diameter than the exterior of said sample introduction column; said bore having a chromatographic surface; said MS transfer column having a first end and a second end; said first end of said MS transfer column being insertable into the mass spectrometer source;
   (b) a means for connecting the second end of said sample introduction column to a carrier gas source;
   (c) an enclosed chamber into which the second end of said MS transfer column and the first end of said sample introduction column may be inserted;
   (d) a means for axially aligning the sample introduction column and MS transfer column;
   (e) a means for applying a vacuum source to said enclosed chamber;
   (f) a means for supporting said sample introduction column at a point outside of said enclosed chamber; and
   (g) a means for moving said sample introduction column along its axis so that the extent to which it is inserted into the MS transfer column may be controlled.

2. The device for analysis of a sample using a mass spectrometer and a sample introduction column as recited in claim 1, wherein the means for moving the sample introduction column along its axis comprises a bellows/micrometer drive mechanism.

3. The device for analysis of a sample using a mass spectrometer and a sample introduction column as recited in claim 1, wherein the means for applying a vacuum source to said enclosed chamber comprises a vacuum outlet having a bore greater in diameter than the bore of the MS transfer column, said vacuum outlet being connected to a vacuum pump.

4. The device for analysis of a sample using a mass spectrometer and a sample introduction column as recited in claim 3, wherein the MS transfer column is thirty cm or less in length and shorter than the sample introduction capillary.

5. The device for analysis of a sample using a mass spectrometer and a sample introduction column as recited in claim 3, wherein the means for moving the sample introduction column along its axis comprises guide rods connected to guide rod supports.

6. The device for analysis of a sample using a mass spectrometer and a sample introduction column as recited in claim 5, wherein the means for connecting the second end of the sample introduction column to a carrier gas source comprises a flow column and the means for supporting the sample introduction column comprises a union, said flow column having a first flow end and a second flow end, said union having a hollow cylindrical bore extending therethrough between a first union end and a second end, said first flow end being inserted into the second union end and said second end of the sample introduction capillary being inserted into the first union end, and said union being slidably movable along the guide rods such that movement of the union results in axial movement of the sample introduction capillary within the MS transfer column.

7. The device for analysis of a sample using a mass spectrometer and a sample introduction column as recited in claim 6, wherein the flow column, the enclosed chamber, the union and the MS transfer column are aligned in a line of sight path and the sample is not exposed to a chemically active surface in the device.

8. The device for analysis of a sample using a mass spectrometer and a sample introduction column as recited in claim 7, wherein the diameters of the flow column and the sample introduction column are different and the bore of the union is tapered so that the inner diameter of the second union end matches the inner diameter of the first flow end and the inner diameter of the first union end matches the inner diameter of the second end of the sample introduction column.

9. The device for analysis of a sample using a mass spectrometer and a sample introduction column as recited in claim 8, wherein the union comprises a single piece.

10. The device for analysis of a sample using a mass spectrometer and a sample introduction column as recited in claim 9, wherein the union is made of nickel and is enclosed by a polyimide resin coating which does not come into contact with the sample during analysis.

11. The device for analysis of a sample using a mass spectrometer and a sample introduction column as recited in claim 10, wherein the union is permanently attached to the sample introduction column.

12. A device for analysis of a sample using a mass spectrometer and a sample introduction column, said sample introduction column having a first end and a second end, said sample being deposited in a thin film on an adsorbent coating on the interior of the first end of the sample introduction column comprising:
   (a) an MS transfer column having a bore greater in diameter than the exterior of said sample introduction column; said bore having a chromatographic surface; said MS transfer column having a first end and a second end; said first end of said MS transfer column being insertable into the mass spectrometer source;
   (b) a flow column for connecting the second end of said sample introduction column to a carrier gas source, said flow column having a first flow end and a second flow end;
   (c) an enclosed chamber into which the second end of said MS transfer column and the first end of said sample introduction column may be inserted;
   (d) a means for axially aligning the sample introduction column and MS transfer column;
   (e) a means for applying a vacuum source to said enclosed chamber;
   (f) guides rods and guide rod supports for moving said sample introduction column along its axis so that the extent to which the sample introduction column is inserted into the MS transfer column may be controlled; and
   (g) a union for supporting said sample introduction column at a point outside of said enclosed chamber, said union having a hollow cylindrical bore extending therethrough between a first union end and a second union end, said first flow end being inserted into the second union end and said second end of the sample introduction capillary being inserted into the first union end, and said union being slidably movable along the guide rods such that movement of the union results in axial movement of the sample introduction capillary within the MS transfer column.

13. The device for analysis of a sample using a mass spectrometer and a sample introduction column as recited in claim 12, wherein the flow column, the enclosed chamber, the union and the MS transfer column are aligned in a line of sight path and the sample is not exposed to a chemically active surface in the device.

14. The device for analysis of a sample using a mass spectrometer and a sample introduction column as recited in claim 13, wherein the means for applying a vacuum source to said enclosed chamber comprises a vacuum outlet having a bore greater in diameter than the bore of the MS transfer column, said vacuum outlet being connected to a vacuum pump.

15. The device for analysis of a sample using a mass spectrometer and a sample introduction column as recited in claim 14, wherein the MS transfer column is thirty cm or less in length and shorter than the sample introduction capillary.

16. The device for analysis of a sample using a mass spectrometer and a sample introduction column as recited in claim 15, wherein the diameters of the flow column and the sample introduction column are different and the bore of the union is tapered so that the inner diameter of the second union end matches the inner diameter of the first flow end and the inner diameter of the first union end matches the inner diameter of the second end of the sample introduction column.

17. The device for analysis of a sample using a mass spectrometer and a sample introduction column as recited in claim 16, wherein the union comprises a single piece.

18. The device for analysis of a sample using a mass spectrometer and a sample introduction column as recited in claim 17, wherein the union is made of nickel and is enclosed by a polyimide resin coating which does not come into contact with the sample during analysis.

19. The device for analysis of a sample using a mass spectrometer and a sample introduction column as recited in claim 18, wherein the union is permanently attached to the sample introduction column.

20. A devie for analysis of a sample using a mass spectrometer and a sample introduction column, said sample introduction column having a first end and a second end, said sample being deposited in a thin film on an adsorbent coating on the interior of the first end of the sample introduction column comprising:

(a) an MS transfer column having a bore greater in diameter than the exterior of said sample introduction column; said bore having a chromatographic surface; said MS transfer column having a first end and a second end; said first end of said MS transfer column being insertable into the mass spectrometer source;

(b) a flow column for connecting the second end of said sample introduction column to a carrier gas source, said flow column having a first flow end and a second flow end;

(c) an enclosed chamber into which the second end of said MB transfer column and the first end of said sample introduction column may be inserted;

(d) a means for axially aligning the sample introduction column and MS transfer column;

(e) a vacuum outlet having a bore greater in diameter than the bore of the MS transfer column by a factor of forty or more, said vacuum outlet being connected to a vacuum pump;

(f) a means for moving said sample introduction column along its axis so that the extent to which it is inserted into the MS transfer column may be controlled; and (g) a union for supporting said sample introduction column at a point outside of said enclosed chamber, said union having a hollow cylindrical bore extending therethrough between a first union end and a second union end, said first flow end being inserted into the second union end and said second end of the sample introduction capillary being inserted into the first union end, said union being slidably movable such that movement of the union results in axial movement of the sample introduction capillary within the MS transfer column, and said flow column, said enclosed chamber, said union and said MS transfer column being aligned in a line of sight path.

21. The device for analysis of a sample using a mass spectrometer and a sample introduction column as recited in claim 20, wherein the MS transfer column is thirty cm or less in length and shorter than the sample introduction capillary and the sample is not exposed to a chemically active surface in the device.

* * * * *